US008343531B2

(12) United States Patent
Morifuji et al.

(10) Patent No.: US 8,343,531 B2
(45) Date of Patent: Jan. 1, 2013

(54) COMPOSITION CONTAINING PEPTIDE AS ACTIVE INGREDIENT

(75) Inventors: Masashi Morifuji, Saitama (JP); Keiko Kurashige, Tokyo (JP); Chiaki Sanbongi, Tokyo (JP)

(73) Assignee: Meiji Co., Ltd., Tokyo (JP)

( * ) Notice: Subject to any disclaimer, the term of this patent is extended or adjusted under 35 U.S.C. 154(b) by 760 days.

(21) Appl. No.: 12/226,480

(22) PCT Filed: Apr. 20, 2007

(86) PCT No.: PCT/JP2007/058620
§ 371 (c)(1),
(2), (4) Date: Jan. 9, 2009

(87) PCT Pub. No.: WO2007/123200
PCT Pub. Date: Nov. 1, 2007

(65) Prior Publication Data
US 2009/0124560 A1    May 14, 2009

(30) Foreign Application Priority Data
Apr. 21, 2006   (JP) ................................. 2006-117439

(51) Int. Cl.
*A23L 1/305* (2006.01)
*A61K 38/05* (2006.01)

(52) U.S. Cl. .......... 424/439; 426/648; 514/5.5; 514/6.8; 514/6.9; 514/21.91

(58) Field of Classification Search ........................ None
See application file for complete search history.

(56) References Cited

U.S. PATENT DOCUMENTS

| | | | | |
|---|---|---|---|---|
| 4,340,592 | A | * | 7/1982 | Adibi .............................. 514/5.5 |
| 5,036,052 | A | * | 7/1991 | Ozeki et al. .................... 514/5.5 |
| 2001/0031729 | A1 | | 10/2001 | Van Loon et al. |
| 2006/0116426 | A1 * | | 6/2006 | Yamaoka et al. ............. 514/561 |
| 2008/0305151 | A1 * | | 12/2008 | Sakai et al. .................... 424/439 |
| 2009/0105125 | A1 * | | 4/2009 | Zhao et al. ........................ 514/4 |
| 2009/0111747 | A1 * | | 4/2009 | Ewart et al. ..................... 514/12 |
| 2009/0170786 | A1 * | | 7/2009 | Greenberg ...................... 514/19 |

FOREIGN PATENT DOCUMENTS

| | | |
|---|---|---|
| CN | 1747727 A | 3/2006 |
| EP | 1 591 116 A1 | 11/2005 |
| JP | 01-228918 | 9/1989 |
| JP | 03-165833 | 7/1991 |
| JP | 04-149139 | 5/1992 |
| JP | 10-084911 | 4/1998 |
| JP | 2000-509267 | 7/2000 |
| JP | 2002-516318 | 6/2002 |
| JP | 2005-289861 | 10/2005 |
| JP | 2005-538704 | 12/2005 |
| JP | 2006-510367 | 3/2006 |
| JP | 2006096747 A * | 4/2006 |
| WO | 01/37850 A2 | 5/2001 |
| WO | 2004/069236 A1 | 8/2004 |
| WO | WO 2006068480 A2 * | 6/2006 |

OTHER PUBLICATIONS

Shepherd, P.R., et al. (1999). *Glucose transporters and insulin action.* The New England Journal of Medicine, 341,4. pp. 248-257.
Bergström, J., et al. (1967). *Diet, muscle glycogen and physical performance.* Acta physiol. scand. 71, pp. 140-150.
Zhang, B., et al. (1999). *Discovery of a small molecule insulin mimetic with antidiabetic activity in mice.* Science, 284, pp. 974-977.
Shepherd, P.R., et al. (1998). *Phosphoinositide 3-kinase: the key switch mechanism in insulin signalling.* Biochem. J., 333, pp. 471-490.
Schnack, et al., "Effects of 8-Wk α-Glucosidase Inhibition on Metabolic Control, C-Peptide Secretion, Hepatic Glucose Output, and Peripheral Insulin Sensitivity in Poorly Controlled Type II Diabetic Patients," Diabetes Care, (1989), vol. 12, No. 8, pp. 537-543.
Reaven, et al., "Effect of Acarbose on Carbohydrate and Lipid Metabolism in NIDDM Patients Poorly Controlled by Sulfonylureas," Diabetes Care, (1990), vol. 13, Suppl. 3, pp. 32-36.
Jenney, et al., "Low-Dose Acarbose Improves Glycemic Control in NIDDM Patients Without Changes in Insulin Sensitivity," Diabetes Care, (1993), vol. 16, No. 2, pp. 499-502.
International Office Action, Application No. 2007800143234, mailed on Apr. 27, 2011.
Official Action, issued on Jun. 12, 2012, in the counterpart Japanese Application No. 2008-512162, eight (8) pages.
Eto, et al., "Angiotensin I Converting Enzyme-inhibitory Dipeptides in an Alkaline Protease Hydrolysate of Whey Protein," Journal of Japan Society of Nutrition and Food Science, (1998), vol. 51, No. 6, pp. 355-359.
Cheung, et al., "Binding of Peptide Substrates and Inhibitors of Angiotensin-converting Enzyme," The Journal of Biological Chemistry, (1980), Vol. 255, No. 2, pp. 401-407.
Izumi, et al., "Insulance Resistance Improving Action of Ace Inhibitors," Endocrinology and Metabolism, (2001), vol. 12, No. 4, pp. 391-397.
Shiuchi, et al., "Elucidation of Mechanism for Tissue-Specific Glucose Uptake-Promoting Action of Ace Inhibitors; Role of Bradykinin and No," Journal of Japan Endocrine Society, (2000), vol. 76, No. 2, p. 468.
Duarte, et al., "Cardiovascular effects of captopril and enalapril in obese Zucker rats," European Journal of Pharmacology, (1999), Vol. 365, No. 2-3, pp. 225-232.

* cited by examiner

*Primary Examiner* — Jeffrey E Russel
(74) *Attorney, Agent, or Firm* — Nath, Goldberg & Meyer; Tanya E. Harkins

(57) ABSTRACT

The invention provides a composition used for promoting glucose uptake, which comprises a peptide having an effect of promoting glucose uptake as the active ingredient, as well as a composition comprising a dipeptide containing leucine and/or isoleucine as the active ingredient. The composition is effective in preventing or treating diabetes mellitus or an elevation of blood glucose level, in promoting glycogen storage, or in enhancing physical strength, enhancing athletic ability, improving endurance performance or relieving fatigue.

20 Claims, No Drawings

COMPOSITION CONTAINING PEPTIDE AS ACTIVE INGREDIENT

This is an National Phase Application filed under 35 U.S.C. §371 as a national stage of PCT/JP2007/058620, with the filing date of Apr. 20, 2007, an application claiming the benefit under 35 USC §119(a) of Japanese Patent Application No. 2006-117439, filed on Apr. 21, 2006, the entire content of which is hereby incorporated by reference in its entirety.

TECHNICAL FIELD

The present invention relates to a composition containing a peptide as an active ingredient. The present invention also relates to a food or a pharmaceutical composition containing the composition. Further, the present invention relates to a process for producing the composition.

BACKGROUND ART

Diabetes mellitus is a generic term of metabolic disorders characterized by persistence of a hyperglycemic state due to the deficiency of insulin action. Diabetes mellitus is caused by combination in any degrees of reduced insulin sensitivity with reduced insulin secretion to cause characteristic abnormalities in carbohydrate, lipid and protein metabolisms. Recently, diabetes mellitus is said to be one of lifestyle-related diseases and is regarded as a disease expected to be ameliorated by appropriate therapy. However, when diabetes mellitus becomes severe, complications such as neuropathy, retinopathy, and nephropathy are generated, and movements in everyday life may be significantly reduced.

Diabetes mellitus is classified roughly into insulin-dependent diabetes mellitus (IDDM) and non-insulin-dependent diabetes mellitus (NIDDM). IDDM is a type of diabetes mellitus in which pancreatic β-cells are necrotized, or arrested functions, by an autoimmune mechanism caused by a virus or the like, thereby failing to synthesize and secrete insulin. NIDDM is a type of diabetes mellitus in which hyperglycemia is manifested due to insufficient insulin secretion and insulin resistance caused by uncertain and diverse factors such as aging and stress. About 90% of patients with diabetes mellitus fall under NIDDM.

In therapy of patients with mild or moderate non-insulin-dependent diabetes mellitus, diet therapy and exercise therapy are mainly adopted. For example, the stabilization of blood glucose level is attempted by calorie restriction in meal and by improvement of carbohydrate metabolism with exercise. From the viewpoint of prevention of diabetes mellitus or prevention of ingravescence thereof, there has been demand for further development of diet therapy with a food capable of preventing diabetes mellitus or preventing ingravescence thereof.

If a rapid increase in blood glucose level after meal and its continuance (hyperglycemia after meal) continue for many years, abnormal glucose tolerance will sooner or later result to exacerbate diabetes mellitus. Exacerbation of diabetes mellitus is accompanied by promotion of angiopathy, which can lead to development of neurosis, nephropathy and retinopathy and to further complications of myocardial infarction and apoplexy. Suppression of hyperglycemia after meal is regarded as effective in treatment of NIDDM, and α-glucosidase inhibitors are used as carbohydrates absorption inhibitors, and medical pharmaceutical preparations such as sulfonylurea agents are used as insulin secretagogues. Under these circumstances, pharmaceutical preparations that prevent diabetes mellitus or prevent ingravescence thereof have also been desired in the field of pharmaceutical preparations.

There is insulin as a biological material that can suppress an elevation of blood glucose level. Insulin is a sole hormone in the living body, which decreases the level of blood glucose, for example by causing promotion of carbohydrate metabolism in the liver and enhancement of glucose uptake into muscle cells and fat cells. The glucose incorporated into muscle or fat cells is metabolized to glycogen to be stored in tissues. Translocation (recruitment), to a cell membrane, of glucose transporter-4 (GLUT-4) present in an intracellular pool can be mentioned as one mode of action of insulin in muscle or fat cells. The signal transduction mechanism involved in glucose uptake in muscle or fat cells by insulin is estimated at present as follows:

That is, insulin binds to an insulin receptor (IR) on a cell membrane and then activates a tyrosine kinase in an intracellular moiety of IR to tyrosine-phosphorylate a family of insulin receptor substrates (IRSs). The tyrosine-phosphorylated IRSs activate phosphatidylinositol 3-kinase (PI3K), followed by some signal transductions, to translocate intracellular latent GLUT-4 to a cell membrane (see, for example, N. Engl. J. Med., 341, 248-257, 1999). This insulin is also used as a pharmaceutical preparation to prevent diabetes mellitus or prevent ingravescence thereof.

As described above, abnormalities in carbohydrate metabolism are related to many lifestyle-related diseases, and thus there is necessity for foods and pharmaceutical preparations aimed at preventing lifestyle-related diseases or preventing ingravescence thereof.

Physical strength, particularly endurance, anti-fatigue strength and fatigue-relieving strength become important in the field of sports. The fatigue of muscles by exercise occurs when glycogen serving as a source of energy production in tissues is consumed to a certain limit. That is, when glycogen in tissues is exhausted, muscles become unable to move. A positive correlation between glycogen stores in tissues and endurance has been reported (see, for example, Acta Physiol. Scand., 71, 140-150, 1967). Accordingly, it is important to increase glycogen stores in tissues in order to enhance endurance, anti-fatigue strength, fatigue-relieving strength, etc.

Under these circumstances, it has been reported as a result of recent studies that for example, substances having an action of promoting glucose uptake into cells are discovered in microorganism-derived, low-molecular substances or in plant extracts (see, for example, Science, 284, 974-977, 1999). In addition, milk whey protein and its hydrolysates for example are reported to have an effect of storing glycogen (see, for example, Japanese Patent Application Laid-Open No. 2005-289861). Further, it has already been reported that milk protein hydrolysates have an action of reducing the level of blood glucose to exert a therapeutic effect on diabetes mellitus (see, for example, Japanese Patent Application Laid-Open z4-149139), and that milk whey protein hydrolysates have an action of regulating blood glucose (see, for example, Japanese Patent Application National Publication (Laid-Open) No. 2006-510367).

DISCLOSURE OF THE INVENTION

In view of these circumstances, the present inventors decided that an object of the present invention is to provide a composition having an effect on at least one of the followings: prevention or treatment of diabetes mellitus or of an elevation of blood glucose level, promotion of glycogen storage, enhancement of physical strength, enhancement of athletic ability, improvement of endurance, and relief from fatigue.

The present inventors also decided that another object of the present invention is to provide a food or a pharmaceutical composition having at least one of the effects mentioned above. Further, the present inventors decided that still another object of the present invention is to provide a process for producing a composition having at least one of the effects mentioned above.

The present inventors made extensive study, and as a result, they found a composition which can reduce the level of blood glucose and promote storage of glycogen, and the present invention was thereby completed.

According to one mode of the present invention, there is provided a composition used for promoting glucose uptake, which comprises a peptide having an effect of promoting glucose uptake as the active ingredient. The "peptide having an effect of promoting glucose uptake" is preferably a dipeptide having leucine and/or isoleucine.

According to another mode of the present invention, there is provided a composition comprising a dipeptide having leucine and/or isoleucine as the active ingredient.

In the present invention, the "composition" encompasses "a peptide itself (a single peptide or a mixture of peptides), "protein hydrolysates", and "mixtures obtained by purifying protein hydrolysates by membrane treatment, solvent fractionation etc."

In any of the modes described above, it is possible to employ at least one dipeptide selected from the group consisting of Ile-Leu, Ile-Trp, Ala-Leu, Val-Leu, Gly-Leu, Asp-Leu, Lys-Ile, Leu-Leu, Ile-Ile, Leu-Ile, Ile-Asn, Leu-Ala, Leu-Glu, Leu-Val and Ile-Val.

By incorporating the composition of the present invention, there can be provided a food or a pharmaceutical composition having an effect on at least one of the followings: prevention or treatment of diabetes mellitus or of an elevation of blood glucose level, promotion of glycogen storage, enhancement of physical strength, enhancement of athletic ability, improvement of endurance, and relief from fatigue.

According to the present invention, there is provided a process for producing a composition comprising a peptide as the active ingredient.

The disclosure of this application is related to the subject matter described in Japanese Patent Application No. 2006-117439 filed Apr. 21, 2006, the disclosure of which is incorporated by reference herein.

BEST MODE FOR CARRYING OUT THE INVENTION

One mode of the composition of the present invention relates to a composition used for promoting glucose uptake, which comprises a peptide having an effect of promoting glucose uptake as the active ingredient. The peptide having an effect of promoting glucose uptake is preferably a dipeptide containing leucine and/or isoleucine. A preferably usable dipeptide is particularly Ile-Leu, Ile-Trp, Ala-Leu, Val-Leu, Gly-Leu, Asp-Leu, Lys-Ile, Leu-Leu, Ile-Ile, Leu-Ile, Ile-Asn, Leu-Ala, Leu-Glu, Leu-Val or Ile-Val.

Another mode of the composition of the present invention relates to a composition comprising a dipeptide containing leucine and/or isoleucine as the active ingredient. The composition in this mode is used for example as a biologically active composition, a nutritional composition, or a functional composition. The composition in this mode can also be used in promoting glucose uptake. A preferably usable dipeptide containing leucine and/or isoleucine is particularly Ile-Leu, Ile-Trp, Ala-Leu, Val-Leu, Gly-Leu, Asp-Leu, Lys-Ile, Leu-Leu, Ile-Ile, Leu-Ile, Ile-Asn, Leu-Ala, Leu-Glu, Leu-Val or Ile-Val.

In any of the modes described above, the active ingredient peptide has a preventive or therapeutic effect on diabetes mellitus or on an elevation of blood glucose level (in this specification, the preventive effect on an elevation of blood glucose level and the effect on reduction of blood glucose level shall be used synonymously with each other unless otherwise noted), an effect on promotion of glycogen storage, or an effect on enhancement of physical strength, enhancement of athletic ability, improvement of endurance, or relief from fatigue. The peptide in the present invention is considered as a biologically active substance similar to insulin, and its working mechanism is estimated to be similar to that of insulin. Insulin used conventionally as a pharmaceutical preparation is a peptide containing a molecular weight of 3,500 or more and can thus not be adsorbed into the body by oral administration. However, the peptide in the present invention, particularly the dipeptide containing leucine and/or isoleucine, is a peptide that can, upon oral administration, exhibit an action of promoting glucose uptake into cells, thereby enabling suppression of an elevation of blood glucose level. Such a peptide does not exert a harmful effect on the human body.

The peptide having an action of promoting glucose uptake can promote glucose uptake into cells such as muscle cells and liver cells, particularly muscle cells. In muscle cells, insulin binds to an insulin receptor, to cause activation of phosphoinositide 3-kinase (PI3K) downstream of an insulin receptor signal, then via several signal transductions, to translocate glucose transporter-4 (GLUT-4) to the surface of a cell. Usually, glucose is then incorporated into the cell via GLUT-4 on the surface of the cell. This pathway is inhibited by a GLUT-4 inhibitor or a PI3K inhibitor.

The glucose uptake-promoting effect of the peptide in the composition of the present invention is suppressed by a GLUT-4 inhibitor or a PI3K inhibitor, as will be shown later in the Examples. Accordingly, it is estimated that the glucose uptake promoted by the peptide is a GLUT-4-mediated action similar to the action of insulin and is also a PI3K-mediated action similar to the action of insulin. As the GLUT-4 inhibitor, cytochalasin B for example is known, and as the PI3K inhibitor, LY294002 (Biochemical Journal, 333, 471-490, 1998) for example is known.

The peptide-containing composition of the present invention can reduce the level of blood glucose. By reducing the level of blood glucose, diabetes mellitus and an elevation of blood glucose level can be prevented or treated.

The composition of the present invention has an action of storing glycogen in tissues. Accordingly, the composition can improve exercise performance, thus making sufficient effectiveness expectable in the field of sports. According to the composition of the present invention, it is possible to enhance endurance performance during exercise, an anti-fatigue action, an ability to relieve from fatigue, physical strength, exercise performance, stamina, and powder to supply energy.

The peptide in the present invention can be synthesized from amino acids, but preferably it can be obtained by hydrolyzing a protein. Accordingly, one example of the composition of the present invention is a hydrolysate containing a peptide obtained by hydrolyzing a protein.

Hydrolysis is preferably hydrolysis with a protease. The starting material that can be used herein include animal proteins and vegetable proteins, and examples thereof include beef, swine meat, chicken meat, egg, soybean, cow milk, peanut, sweet corn, and wheat. In the present invention, casein, soybean protein, wheat gluten, milk whey protein, and beef are preferably used, among which particularly milk whey protein is preferably used. The milk whey protein that can be used therein includes, for example, mixtures obtained from cheese whey or casein whey by filtration such as ultrafiltration or nanofiltration, as well as β-lactoglobulin, α-lactalbumin and lactoferrin isolated and purified therefrom.

Conditions for treatment with an enzyme, acid or alkali in protein hydrolysis (for example, substrate concentration, enzyme amount, treatment temperature, pH, and time) can be appropriately established. The enzyme used in protein hydrolysis is preferably harmless from the viewpoint of food hygiene, and examples of such enzymes include proteases derived from microorganisms belonging to *Bacillus* or *Aspergillus*, plant-derived proteases such as papaya-derived papain and pineapple-derived bromelain, and animal-derived proteases such as pancreatin and trypsin, and these enzymes can be used alone or as a combination.

For example, when Ile-Leu is obtained, a combination of a protease derived from *Bacillus* and a protease from *Aspergillus* is preferably used in hydrolysis; when Ile-Trp is obtained, it is preferable that a starting protein is reacted with trypsin and then reacted with a protease derived from *Aspergillus*; when Val-Leu, Lys-Ile, Ile-Ile, Leu-Ile, Ile-Asn, Leu-Ala, Leu-Glu, and Ile-Val are obtained, a protease derived from *Aspergillus* is preferably used; when Ala-Leu and Asp-Leu are obtained, it is preferable that a protein is reacted with trypsin and then reacted with a protease derived from *Bacillus*; and when Gly-Leu, Leu-Leu and Leu-Val are obtained, it is preferable that a protein is reacted with pepsin and then reacted with a protease derived from *Aspergillus*.

In the case of hydrolysis with a protease, for example, the treatment temperature is preferably 35 to 55° C., the treatment time is preferably 3 to 9 hours, and the amount of the enzyme used is 0.5 to 10 g per 100 g protein.

From a protein hydrolysate, a highly pure peptide having an action of promoting glucose uptake can be isolated and purified by purification methods such as adsorbent treatment, membrane separation, solvent fractionation, and column chromatographic procedures using an ordinary used resin.

Prior to isolation and purification, the peptide may be extracted from a protein hydrolysate. The solvent used in extracting the peptide is preferably water, ethanol, methanol, acetone, or a mixed solvent thereof. For example, 90 vol % aqueous ethanol can be used as the solvent.

Although the ratio of the solvent to the protein hydrolysate in extraction is not particularly limited, the weight ratio of the solvent to the (dried) protein hydrolysate is preferably 2 to 1,000, particularly 5 to 100, from the viewpoint of extraction operation and efficiency. The extraction temperature is conveniently in the range of "room temperature" to "the boiling point of the solvent at normal pressures". The extraction time varies depending on the extraction temperature, but is preferably in the range of several hours to 2 days. By such operation, a purified peptide can be obtained as a solvent extract. Accordingly, one example of the composition of the present invention includes a solvent extract containing a purified peptide. The solvent extract is used preferably in a lyophilized state.

When a protein hydrolysate or its solvent extract is fractionated by adsorption chromatography, there is for example the following method. First, a lyophilized protein hydrolysate or its solvent extract is dissolved in a small amount of solvent such as water, methanol or ethanol, or a mixed solvent thereof. Then, the resulting solution is applied onto a column to adsorb the peptide onto an adsorbent. Thereafter, the column is sufficiently washed with water, and the peptide may be eluted with a hydrophilic solvent such as methanol, ethanol or acetone, or a mixed solvent thereof. In place of the adsorption column chromatography, chromatography in another separation mode may be used. The peptide isolated and purified to a higher degree can be obtained by a combination of column chromatography in two or more adsorption and/or column chromatography in another separation mode. The adsorption bent-charged chromatography includes Sephadex LH-20 (manufactured by Pharmacia, Sweden), DIAION HP20 (manufactured by Mitsubishi Chemical Corporation), Develosil ODS (manufactured by Nomura Chemical Co., Ltd.), ODS-A (manufactured by YMC), ODS-AQ (manufactured by YMC), MCI-GEL (manufactured by Mitsubishi Chemical Corporation), MCI-CHP20 (manufactured by Mitsubishi Chemical Corporation), Sepabeads HP1MG (manufactured by Mitsubishi Chemical Corporation), and Toyopearl HW40F (manufactured by Tosoh Corporation).

The peptide thus isolated and purified can also be used as the composition of the present invention. Alternatively, a peptide mixture, that is, a protein hydrolysate before isolation and purification or a solvent extract may be used directly or after lyophilization as the composition of the present invention. Depending on the case, the composition of the present invention can be ingested as it is.

The composition of the present invention may contain known substances in addition to the active ingredient peptide. For example, the composition of the present invention may contain other peptides generated by hydrolyzing various proteins usable as the starting material, or a catalyst used in hydrolysis. The composition of the present invention may also contain various kinds of carbohydrates to increase the amount of glucose incorporated into cells.

The composition of the present invention obtained in the manner described above can be incorporated into general foods (including drinks). Foods blended with the composition of the present invention are used as foods for preventing or treating diabetes mellitus or an elevation of blood glucose level. The foods can be similarly used for enhancing the storage of glycogen in tissues to improve exercise performance. Similarly, the foods can also be used for enhancing physical strength, enhancing athletic ability, improving endurance performance, and relieving fatigue.

The food of the present invention has an action of promoting glucose uptake into muscle cells and an action of promoting glycogen storage, and can thus be provided as a daily ingested food, a health food taken as a supplement, or a functional food. Then, the food of the present invention is a food for suppression of an elevation of blood glucose level and for prevention or treatment of diabetes mellitus, a food adapted to consumers who desire enhancement of physical strength, prevention of reduction in physical strength, enhancement of exercise performance, improvement of endurance, and recovery from fatigue, or a food adapted to consumers who worry about these symptoms. Accordingly, the food of the present invention can be provided as a food for specified health use or as a food for patients. Further, the food of the present invention, when used for nonhuman mammals, can be used as feed.

The form of the food of the present invention is not particularly limited. Specific examples of the food of the present invention include drinks, powdered drinks, conc. drinks, tablets, baked goods, soups, hamburgers, powdered foods, capsulated foods, jelly, curry, bread, sausages, yogurts, cheeses, chocolates, chewing gums, jams, and ice creams.

The peptide having an effect of promoting glucose uptake is preferably water-soluble. The dipeptide containing leucine and/or isoleucine is water-soluble. The water-soluble dipeptide can be added widely to general foods. For example, the peptide can be taken in an amount of 10 mg per day by daily drinking about 1 L of tea blended with at least 0.001% by weight of the water-soluble peptide. For suppressing an elevation of blood glucose level, it is preferable that the peptide is incorporated into a food depending on the activity of the peptide to be used, and the amount of the peptide to be ingested is increased or decreased appropriately in the range of 0.1 to 10,000 mg/day in terms of the amount of pure peptide.

The composition of the present invention can also be used as a pharmaceutical composition such as an inhibitor of elevation of blood glucose level or an agent for preventing or treating diabetes mellitus. The composition of the present invention can also be used as a glycogen storage promoter for diseases or symptoms which can be treated, prevented or ameliorated by promotion of glycogen storage. Further, the composition of the present invention can be used as a pharmaceutical composition such as a physical strength enhancer, an athletic ability enhancer, an endurance improver, or a fatigue reliever.

The pharmaceutical composition is administered mainly in the form of an oral agent. Carriers that can be used in the oral agent include, for example, an excipient, a binder, a diluent, an additive, a flavor, a buffer, a thickener, a coloring agent, a stabilizer, an emulsifier, a dispersant, a suspending agent, and a preservative. Specific examples of these carriers include magnesium carbonate, magnesium stearate, talc, refined sugar, lactose, pectin, dextrin, starch, gelatin, tragacanth, methyl cellulose, carboxymethylcellulose sodium, low-melting wax, and cacao butter. Depending on use etc. of the oral agent, these carriers may be used alone or as a mixture thereof.

When the pharmaceutical composition of the present invention is used as an oral agent such as an inhibitor of elevation of blood glucose level, an agent for preventing or treating diabetes mellitus, or an improver of glycogen storage, the amount of the composition administered may appropriately vary depending on the age, symptoms etc. of the patient. Generally, the pharmaceutical composition is used preferably in the range of 0.1 to 10,000 mg/day in terms of the amount of pure peptide.

Other components that can be incorporated into the food or pharmaceutical composition of the present invention include, for example, carbohydrates, proteins, amino acids, minerals and/or vitamins. The carbohydrates include polysaccharides such as starch and corn starch, and other saccharides such as dextrin, sucrose, glucose and fructose. The proteins may be animal proteins, vegetable proteins, or mixtures thereof, and examples include milk protein, soybean protein, and egg protein. The amino acids include essential amino acids such as leucine, isoleucine, valine, tryptophan, phenylalanine, lysine, threonine, methionine and histidine, and nonessential amino acids such as glutamine, glycine, alanine, serine, aspartic acid, glutamic acid, asparagine, arginine, cystine, tyrosine, proline, hydroxyproline, ornithine and taurine. The minerals include, but are not limited to, calcium, magnesium and iron. Further examples of minerals include sodium, potassium and other nutrient essential elements such as zinc, copper, chromium, selenium, manganese and molybdenum. The vitamins include, but are not limited to, nutritionally essential vitamins such as vitamin A, vitamin B1, vitamin B2, vitamin B6, vitamin B12, vitamin C, vitamin D, vitamin E, niacin, pantothenic acid, folic acid, and coenzyme Q10.

The peptide as the active ingredient in the composition of the present invention has sufficient effectiveness as an active substance showing an action of suppressing an elevation of blood glucose level or an action of enhancing the storage of glycogen. The composition of the present invention has an effect of prevention or treatment of diabetes mellitus or an elevation of blood glucose level, promotion of glycogen storage, enhancement of physical strength, enhancement of exercise performance, improvement of endurance, or recovery from fatigue. By incorporating the composition of the present invention, there can be provided a food or a pharmaceutical composition which exhibits an excellent effect on prevention or treatment of diabetes mellitus or on an elevation of blood glucose level, on promotion of glycogen storage, or on enhancement of physical strength, enhancement of exercise performance, improvement of endurance, or recovery from fatigue.

EXAMPLES

Hereinafter, the present invention is described in more detail by reference to production examples of peptides as the active ingredient, various biological test examples, pharmaceutical examples, etc. Of course, the present invention is not limited to these examples. In the present invention, "%" and "parts" refer to "% by weight" and "parts by weight", respectively.

Production Example 1

50 g of casein, soybean protein, wheat gluten, milk whey protein, or beef was dissolved in 1 L water, respectively. Each solution was adjusted to pH 7.0, then heated to 50° C. and kept warm. 500 mg of *Bacillus*-derived protease (Protease M Amano manufactured by Amano Enzyme Inc.) and 500 mg of *Aspergillus*-derived protease (Protease N Amano manufactured by Amano Enzyme Inc.) were added to each solution, incubated for 8 hours and then heated for 10 minutes to inactivate the proteases.

The resulting solution was lyophilized to form powder. The powder was diluted 1000-fold (volume ratio) in 0.1% trifluoroacetic acid (TFA) solution, and the contents of Ile-Leu, Ile-Trp, Ala-Leu, Val-Leu, Gly-Leu, Asp-Leu, Lys-Ile, Leu-Leu, Ile-Ile, Leu-Ile, Ile-Asn, Leu-Ala, Leu-Glu, Leu-Val and Ile-Val were quantified using LC/MS analysis under the following conditions.

The amount (mg) of each peptide per 1 g protein is shown in Table 1. The peptides shown in Table 1 were obtained from casein, soybean protein, wheat gluten, milk whey protein, and beef.

Analysis Conditions

Column: Develosil ODS-HG-3 (15 mm×2 mm)

Mobile phase: Solution A: 0.05% TFA solution (v/v)

Solution B: 0.05% TFA in acetonitrile (v/v)

Develosil ODS-HG-3 column was eluted with a linear gradient of each of Solution A and Solution B. The column was eluted with 3% Solution B (v/v) at 0 min, and the concentration of Solution B was increased to 20% (v/v) at 40 min.

Column temperature: 35° C.

Flow rate: 0.2 mL/min

MS Conditions

Ionization: API-ES positive

Drying gas: 10 L/min at 350° C.

Nebulizer: 25 psig

Fragmentor: 30 V

EM gain: 1

TABLE 1

|  | Ile-Leu | Ile-Trp | Ala-Leu | Val-Leu | Gly-Leu | Asp-Leu | Lys-Ile | Leu-Leu |
|---|---|---|---|---|---|---|---|---|
| Casein hydrolysate | 0.64 | 0 | 1.27 | 2.98 | 0.48 | 0.09 | 3.50 | 0.80 |
| Soybean protein hydrolysate | 1.98 | 0.12 | 2.30 | 3.49 | 0.44 | 0.22 | 3.59 | 0.28 |
| Wheat gluten hydrolysate | 2.22 | 0 | 1.01 | 2.56 | 0.32 | 0.00 | 2.38 | 0.12 |
| Milk whey protein hydrolysate | 3.82 | 0.37 | 1.53 | 4.70 | 0.36 | 0.09 | 4.82 | 1.56 |
| Beef hydrolysate | 2.45 | 0.11 | 2.71 | 3.40 | 0.48 | 0.44 | 5.26 | 0.40 |

|  | Ile-Ile | Leu-Ile | Ile-Asn | Leu-Ala | Leu-Glu | Leu-Val | Ile-Val |
|---|---|---|---|---|---|---|---|
| Casein hydrolysate | 0.07 | 0.13 | 4.63 | 0.36 | 3.95 | 0.49 | 1.80 |
| Soybean protein hydrolysate | 0.11 | 0.09 | 3.58 | 0.46 | 3.50 | 0.16 | 0.48 |
| Wheat gluten hydrolysate | 0.40 | 0.04 | 0.39 | 0.13 | 2.26 | 0.09 | 0.24 |
| Milk whey protein hydrolysate | 0.04 | 0.18 | 3.98 | 0.74 | 4.35 | 0.34 | 0.24 |
| Beef hydrolysate | 0.27 | 0.11 | 1.73 | 0.51 | 4.58 | 0.18 | 0.78 |

(mg/g protein)

Production Example 2

50 g of milk whey protein was dissolved in 1 L water. 1) 500 mg of *Bacillus*-derived protease (Protease M Amano manufactured by Amano Enzyme Inc.), 2) 500 mg of *Aspergillus*-derived protease (Protease N Amano manufactured by Amano Enzyme Inc.), 3) 500 mg of trypsin (manufactured by Novo Inc.), 4) 500 mg of pepsin (manufactured by Wako Pure Chemical Industries, Ltd.), 5) 500 mg of Flavorzyme (manufactured by Novo Inc.), 6) 500 mg of *Aspergillus*-derived protease (Umamizyme manufactured by Amano Enzyme Inc.), 7) 500 mg of *Aspergillus*-derived protease (Protease A Amano manufactured by Amano Enzyme Inc.), and 8) 500 mg of *Aspergillus*-derived protease (Protease P Amano manufactured by Amano Enzyme Inc.) were added singly or as a mixture thereof to the solution, to hydrolyze the milk whey protein (Table 2). After the inactivation of the proteases by heating, each of the resulting solutions was lyophilized to form powder. The powder was diluted 1000-fold (volume ratio) in 0.1% trifluoroacetic acid solution, and the contents of Ile-Leu, Ile-Trp, Ala-Leu, Val-Leu, Gly-Leu, Asp-Leu, Lys-Ile, Leu-Leu, Ile-Ile, Leu-Ile, Ile-Asn, Leu-Ala, Leu-Glu, Leu-Val and Ile-Val were quantified using LC/MS analysis under the conditions shown above.

The results are shown in Table 2. A protein hydrolysate containing the highest content of Ile-Leu was obtained by reaction with a combination of 1) *Bacillus*-derived protease and 2) *Aspergillus*-derived protease. A protein hydrolysate containing the highest content of Ile-Trp was obtained by reaction with 3) trypsin and then by reaction with 2) *Aspergillus*-derived protease.

A protein hydrolysate containing a high content of Val-Leu, Lys-Ile, Ile-Ile, Leu-Ile, Ile-Asn, Leu-Ala, Leu-Glu, or Ile-Val was obtained by reaction with 6) *Aspergillus*-derived protease; a protein hydrolysate containing a high content of Ala-Leu or Asp-Leu was obtained by reaction with 3) trypsin and then by reaction with 1) *Bacillus*-derived protease; and a protein hydrolysate containing a high content of Gly-Leu, Leu-Leu or Leu-Val was obtained by reaction with 4) pepsin and then by reaction with 2) *Aspergillus*-derived protease.

TABLE 2

| Enzymes and reaction conditions used | Ile-Leu | Ile-Trp | Ala-Leu | Val-Leu | Gly-Leu | Asp-Leu | Lys-Ile | Leu-Leu |
|---|---|---|---|---|---|---|---|---|
| Reaction with the enzyme (1) (pH 7.0, 50° C., 8 hours) | 2.39 | 0.19 | 0.64 | 2.35 | 0.13 | 0.11 | 1.97 | 0.67 |
| Reaction with the enzyme (2) (pH 7.0, 50° C., 8 hours) | 3.74 | 0.81 | 1.98 | 2.13 | 0.36 | 0.01 | 1.07 | 8.20 |
| Reaction with the enzyme (3) (pH 7.0, 37° C., 8 hours) | 0.00 | 0.00 | 0.06 | 0.00 | 0.00 | 0.02 | 0.17 | 0.00 |
| Reaction with the enzyme (4) (pH 2.5, 37° C., 8 hours) | 0.11 | 0.00 | 0.00 | 0.00 | 0.00 | 0.00 | 0.00 | 0.00 |
| Reaction with the enzymes (1) and (2) (pH 7.0, 50° C., 8 hours) | 3.82 | 0.37 | 1.53 | 4.70 | 0.36 | 0.09 | 4.82 | 1.56 |
| Reaction with the enzyme (3) (pH 7.0, 37° C., 4 hours) and subsequent reaction with the enzyme (1) (pH 7.0, 50° C., 4 hours) | 3.16 | 0.21 | 4.77 | 5.33 | 0.60 | 1.36 | 4.84 | 1.07 |
| Reaction with the enzyme (3) (pH 7.0, 37° C., 4 hours) and subsequent reaction with the enzyme (2) (pH 7.0, 50° C., 4 hours) | 3.57 | 1.01 | 2.04 | 2.60 | 0.44 | 0.05 | 0.74 | 4.89 |
| Reaction with the enzyme (4) (pH 7.0, 37° C., 4 hours) and subsequent reaction with the enzyme (1) (pH 7.0, 50° C., 4 hours) | 1.47 | 0.19 | 0.75 | 4.92 | 0.34 | 0.06 | 0.54 | 2.21 |
| Reaction with the enzyme (4) (pH 7.0, 37° C., 4 hours) and subsequent reaction with the enzyme (2) (pH 7.0, 50° C., 4 hours) | 2.86 | 0.84 | 2.28 | 3.90 | 0.63 | 0.14 | 0.81 | 13.37 |
| Reaction with the enzyme (5) (pH 7.0, 50° C., 6 hours) | 0.62 | 0.03 | 0.35 | 1.58 | 0.17 | 0.04 | 1.54 | 0.20 |
| Reaction with the enzyme (6) (pH 7.0, 50° C., 6 hours) | 2.78 | 0.23 | 1.09 | 6.25 | 0.36 | 0.14 | 6.45 | 1.85 |
| Reaction with the enzyme (7) (pH 7.0, 50° C., 6 hours) | 2.17 | 0.27 | 0.64 | 4.23 | 0.18 | 0.06 | 2.72 | 2.22 |
| Reaction with the enzyme (8) (pH 7.0, 50° C., 6 hours) | 1.85 | 1.00 | 0.66 | 5.19 | 0.33 | 0.05 | 3.83 | 1.74 |

| Enzymes and reaction conditions used | Ile-Ile | Leu-Ile | Ile-Asn | Leu-Ala | Leu-Glu | Leu-Val | Ile-Val |
|---|---|---|---|---|---|---|---|
| Reaction with the enzyme (1) (pH 7.0, 50° C., 8 hours) | 0.02 | 0.03 | 2.73 | 1.22 | 1.90 | 0.10 | 0.09 |
| Reaction with the enzyme (2) (pH 7.0, 50° C., 8 hours) | 0.01 | 0.09 | 2.40 | 1.77 | 1.08 | 1.60 | 0.15 |

TABLE 2-continued

| | | | | | | | |
|---|---|---|---|---|---|---|---|
| Reaction with the enzyme (3) (pH 7.0, 37° C., 8 hours) | 0.00 | 0.00 | 0.03 | 0.00 | 0.02 | 0.00 | 0.00 |
| Reaction with the enzyme (4) (pH 2.5, 37° C., 8 hours) | 0.00 | 0.00 | 0.00 | 0.00 | 0.00 | 0.00 | 0.00 |
| Reaction with the enzymes (1) and (2) (pH 7.0, 50° C., 8 hours) | 0.04 | 0.18 | 3.98 | 0.75 | 4.35 | 0.34 | 0.24 |
| Reaction with the enzyme (3) (pH 7.0, 37° C., 4 hours) and subsequent reaction with the enzyme (1) (pH 7.0, 50° C., 4 hours) | 0.08 | 0.05 | 1.65 | 0.83 | 4.82 | 0.13 | 0.15 |
| Reaction with the enzyme (3) (pH 7.0, 37° C., 4 hours) and subsequent reaction with the enzyme (2) (pH 7.0, 50° C., 4 hours) | 0.02 | 0.06 | 1.61 | 1.96 | 0.71 | 2.38 | 0.19 |
| Reaction with the enzyme (4) (pH 7.0, 37° C., 4 hours) and subsequent reaction with the enzyme (1) (pH 7.0, 50° C., 4 hours) | 0.00 | 0.05 | 1.59 | 2.80 | 0.62 | 0.22 | 0.17 |
| Reaction with the enzyme (4) (pH 7.0, 37° C., 4 hours) and subsequent reaction with the enzyme (2) (pH 7.0, 50° C., 4 hours) | 0.10 | 0.16 | 2.82 | 3.08 | 0.97 | 2.89 | 0.47 |
| Reaction with the enzyme (5) (pH 7.0, 50° C., 6 hours) | 0.02 | 0.02 | 1.64 | 1.05 | 1.40 | 0.04 | 0.16 |
| Reaction with the enzyme (6) (pH 7.0, 50° C., 6 hours) | 0.46 | 0.20 | 4.93 | 3.93 | 5.87 | 0.42 | 1.37 |
| Reaction with the enzyme (7) (pH 7.0, 50° C., 6 hours) | 0.04 | 0.06 | 3.23 | 2.97 | 2.48 | 0.25 | 0.28 |
| Reaction with the enzyme (8) (pH 7.0, 50° C., 6 hours) | 0.02 | 0.02 | 3.70 | 3.54 | 3.56 | 0.15 | 0.14 |

(mg/g protein)

Production Example 3

50 g of milk whey protein was dissolved in 1 L water. The solution was adjusted to pH 7.0, then heated to 50° C. and kept warm. 500 mg of *Bacillus*-derived protease (Protease M Amano manufactured by Amano Enzyme Inc.) and 500 mg of *Aspergillus*-derived protease (Protease N Amano manufactured by Amano Enzyme Inc.) were added to the solution, incubated for 8 hours and then heated for 10 minutes to inactivate the proteases. Then, the resulting solution was powdered by lyophilization to give a whey protein hydrolysate. From 10 g of the whey protein hydrolysate, Ile-Leu and Ile-Trp were extracted with 1 L of 0%, 50%, 60%, 70%, 80%, 90% or 95% ethanol (% by volume of ethanol based on the whole of the aqueous ethanol solution). Each of the extracts thus obtained was concentrated in a concentrating evaporator and lyophilized to form powder. The resulting powder was diluted 1000-fold (volume ratio) in 0.1% trifluoroacetic acid solution, and the contents of Ile-Leu and Ile-Trp were quantified using LC/MS analysis under the conditions described above.

The results are shown in Table 3. The extract with 90% ethanol contained the highest amounts of Ile-Leu and Ile-Trp.

TABLE 3

| Condition | Ile-Leu | Ile-Trp |
|---|---|---|
| 0% | 3.82 | 0.37 |
| 50% | 3.65 | 0.35 |
| 60% | 3.65 | 0.35 |
| 70% | 3.65 | 0.36 |
| 80% | 3.67 | 0.42 |
| 90% | 7.42 | 0.72 |
| 95% | 1.82 | 0.20 |

(mg/g protein)

Example 1

Tablets

The following components were taken in predetermined amounts, mixed uniformly and compression-molded to form tablets of 7 mm in diameter each weighing 150 mg.

Isoleucyl leucine (glucose uptake-promoting dipeptide): 30 parts
Glutamine: 5 parts
Valine: 5 parts
Leucine: 7 parts
Isoleucine: 3 parts
Corn starch: 19 parts
Crystalline cellulose: 30 parts
Magnesium stearate: 1 part Example 2

Food

The following components were taken in predetermined amounts and homogenized to form the food of the present invention.
glucose uptake-promoting peptide-containing protein hydrolysate (powder) prepared in Production Example 1: 90 Parts
Glutamine: 2 parts
Ferric pyrophosphate: 1 part
Corn starch: 7 parts Example 3

Tablet Confectionery

The food in Example 2 was used in the following composition to produce tablet confectionery in a usual manner.
Granulated sugar: 52 parts
Concentrated juice: 5 parts
Citric acid: 6 parts
Flavor: 2 parts
Emulsifying agent: 3 parts
The food in Example 2: 32 parts Biological Test Example 1

Influence on the Rate of Glucose Uptake into Isolated Muscles

Epitrochlearis muscles were excised from male Wister rats (each weighing 120 g) (16 rats) under pentobarbital anesthesia carefully so as not to hurt the epitrochlearis muscles. The epitrochlearis muscles were incubated at 35° C. for 1 hour in KRH buffer (136 mM NaCl, 4.7 mM KCl, 1.25 mM $CaCl_2$, 1.25 mM $MgSO_4 \cdot 7H_2O$, 20 mM Hepes, 1 mg/mL BSA, pH 7.4; referred to hereinafter as KRH buffer) containing 0.1% bovine serum albumin (BSA), 8 mM glucose and 32 mM mannitol, in 5% $CO_2$/95% $O_2$. Thereafter, the epitrochlearis muscles were removed and incubated (8 samples per group) at 30° C. for 30 minutes in KRH buffer containing 0.1% BSA, 40 mM mannitol, and 1 mM Ile-Leu (Kokusan Chemical Co., Ltd.), 1 mM Ile-Trp (Kokusan Chemical Co., Ltd.), or the milk whey protein hydrolysate containing 1 mM leucine in terms of amino acid, produced in Production Example 1, in 5% $CO_2$/95% $O_2$. Then, the epitrochlearis muscles were removed and incubated at 30° C. for accurately 20 minutes in KRH buffer containing 0.1% BSA, 32 mM mannitol and 8 mM 2-deoxyglucose, in 5% $CO_2$/95% $O_2$. Immediately after incubation for accurately 20 minutes, the epitrochlearis muscles were frozen with liquid nitrogen. Thereafter, the frozen epitrochlearis muscles were homogenized in 0.3 M perchloric acid aqueous solution, and after the resulting suspension was neutralized, the amount of 2-deoxyglucose-6-phosphate in the muscles was quantified by an enzymatic method to determine the rate of glucose uptake.

The rate of glucose uptake (average value±standard deviation) is shown in Table 4. All of Ile-Leu, Ile-Trp, and the protein hydrolysate had an action of incorporating glucose into the isolated muscles.

TABLE 4

|  | Rate of glucose uptake into isolated skeletal muscles (μmol/min/g muscle) |
| --- | --- |
| Control (with no sample added) | 0.95 ± 0.10 |
| 1 mM Ile-Leu | 1.88 ± 0.40* |
| 1 mM Ile-Trp | 1.92 ± 0.31* |
| 130 mg/L protein hydrolysate | 1.45 ± 0.20* |

*There is a significant difference within 5%.

Biological Test Example 2

Influence of PI3K Inhibitor and GLUT-4 Inhibitor on the Rate of Glucose Uptake into Isolated Muscles Epitrochlearis muscles were excised from male Wister rats (each weighing 120 g) (8 samples per group) under pentobarbital anesthesia carefully so as not to hurt the epitrochlearis muscles. The epitrochlearis muscles were incubated at 35° C. for 1 hour in KRH buffer containing 0.1% BSA, 8 mM glucose and 32 mM mannitol, in 5% $CO_2$/95% $O_2$. Thereafter, the epitrochlearis muscles were removed and incubated at 30° C. for 30 minutes in KRH buffer containing 0.1% BSA, 40 mM mannitol, and 1 mM Ile-Leu (Kokusan Chemical Co., Ltd.), 1 mM Ile-Leu+10 μM LY294002 (Sigma) or 1 mM Ile-Leu+70 μM cytochalasin B (Sigma) in 5% $CO_2$/95% $O_2$. Then, the epitrochlearis muscles were removed and incubated at 30° C. for accurately 20 minutes in KRH buffer containing 0.1% BSA, 32 mM mannitol and 8 mM 2-deoxyglucose, in 5% $CO_2$/95% $O_2$. Immediately after incubation for accurately 20 minutes, the epitrochlearis muscles were frozen with liquid nitrogen. Thereafter, the frozen epitrochlearis muscles were homogenized in 0.3 M perchloric acid aqueous solution, and after the resulting suspension was neutralized, the amount of 2-deoxyglucose 6-phosphate in the muscles was quantified by an enzymatic method to determine the rate of glucose uptake.

The rate of glucose uptake (average value±standard deviation) is shown in Table 5. The action of Ile-Leu on glucose uptake was inhibited by adding the PI3K inhibitor, LY294002 and the GLUT-4 inhibitor, cytochalasin B. This indicates that Ile-Leu translocates GLUT4 via PI3K onto a cell membrane, to promote the GLUT-4-mediated action of glucose uptake into isolated muscles.

TABLE 5

|  | Rate of glucose uptake into isolated skeletal muscles (μmol/min/g muscle) |
| --- | --- |
| Control (with no sample added) | 0.95 ± 0.10 |
| 1 mM Ile-Leu | 1.88 ± 0.40* |
| 1 mM Ile-Leu + LY294002 | 0.71 ± 0.13 |
| 1 mM Ile-Leu + cytochalasin B | 0.18 ± 0.06 |

*There is a significant difference within 5%.

Biological Test Example 3

Oral Glucose Tolerance Test

Male Wister rats each weighing about 360 g (6 rats per group) were used. The rats were fasted for 18 hours and then administered with 30% glucose aqueous solution in a dose of 2.0 g/kg body weight (BW). As a test substance group, the milk whey protein hydrolysate prepared in Production Example 1, or Ile-Leu, added to 30% glucose aqueous solution, was administered in a dose of 0.1 g/kg body weight (BW). After 30, 60, 90, 120 and 180 minutes, blood was collected from a rat tail vein and measured for its blood glucose level with Diasensor (manufactured by ARKRAY, Inc.).

A change in blood glucose level (average value±standard deviation) is shown in Table 6. Blood glucose can be significantly prevented from increasing by administration of the glucose solution to which the protein hydrolysate or Ile-Leu had been added, as compared with administration of the solution of glucose alone.

TABLE 6

|  | Blood glucose level (mg/100 mL) | | | | | |
| --- | --- | --- | --- | --- | --- | --- |
|  | 0 minute | 30 minutes | 60 minutes | 90 minutes | 120 minutes | 180 minutes |
| Glucose | 0 ± 0 | 62 ± 4 | 61 ± 4 | 57 ± 4 | 27 ± 6 | 5 ± 1 |
| Glucose + protein hydrolysates | 0 ± 0 | 59 ± 7 | 56 ± 2 | 42 ± 3* | 16 ± 4 | 3 ± 1 |
| Glucose + Ile-Leu | 0 ± 0 | 44 ± 8* | 57 ± 7 | 35 ± 4* | 19 ± 3 | 1 ± 3 |

*There is a significant difference within 5%.

Biological Test Example 4

Test for Confirmation of Preventive Effect on Development of Diabetes Mellitus in Model Mice with Type 2 Diabetes Mellitus Ten-week-old model male type 2 diabetic KK-Ay mice (CLEA Japan, Inc.) were fed for 3 weeks with freely given water and diet (8 mice per group). As the feed, 25% casein feed (in accordance with AIN93G), or 25% casein feed to which the milk whey protein hydrolysate prepared in Production Example 1 had been added in an amount of 3%, was given to the mice. Before and 3 weeks after feeding, blood was collected from a mouse tail vein and measured for its blood glucose level.

The level of blood glucose (average value±standard deviation) is shown in Table 7. The mice given the casein diet elevated the level of blood glucose to aggravate diabetes mellitus. On the other hand, the mice given the casein diet to which the milk whey protein hydrolysate had been added inhibited an elevation of blood glucose significantly.

[Table 7]

TABLE 7

| | Blood glucose level (mg/100 mL) | |
|---|---|---|
| | Week 0 | Week 3 |
| Casein diet | 395 ± 42 | 511 ± 28 |

Biological Test Example 5

Test for Confirmation of Glycogen Storage Effect

Male Wister rats (8 animals per group) were fed for 1 week with freely given water and diet. On the 1st to 6th days in breeding, the rats were subjected to loading by swimming training for 6 hours per day. On the day (7th day) before sacrifice, each rat was given 18 g restricted diet. Then, each rat with a weight weighing 2% of the body weight was subjected to glycogen depletion exercise by swimming for 4 hours. Thereafter, the rat was allowed to ingest 25% casein diet (in accordance with AIN93G) as the control, or 25% casein diet whose casein had been replaced by the milk whey protein hydrolysate prepared in Production Example 1. Twelve hours after ingestion, the rat was sacrificed under anesthesia with ether, and the liver and muscles were excised. Immediately, the excised organs were used to analyze the amount of glycogen therein.

The amount of glycogen (average value±standard deviation) is shown in Table 8. The milk whey protein hydrolysate had a glycogen storage-promoting action.

TABLE 8

| | Glycogen content (mmol/g tissue) | |
|---|---|---|
| | Liver | Muscle |
| Control diet | 636 ± 18 | 58 ± 2 |
| Protein hydrolysate feed | 692 ± 24* | 66 ± 2* |

*There is a significant difference within 5%.

Biological Test Example 6

Influence on the Rate of Glucose Uptake into Muscle Cells

Rat L6 myotubes were cultured in an Eagle medium containing 10% bovine serum ($\alpha$-MEM) in a Petri dish coated with type 1 collagen in 5% $CO_2$/95% $O_2$. The cells were recovered by trypsin treatment in a usual manner and seeded at a density of 50,000 cells/well on a 48-well plate coated with type 1 collagen, and cultured for 3 days to make the cells confluent. After the medium was removed, 500 µL of an Eagle medium containing 2% bovine serum ($\alpha$-MEM) was added to each well, and then the cells were cultured for 5 days thereby inducing differentiation. Each well was washed with 500 µL KRH buffer (136 mM NaCl, 4.7 mM KCl, 1.25 mM $CaCl_2$, 1.25 mM $MgSO_4 \cdot 7H_2O$, 20 mM Hepes, 1 mg/mL BSA, pH 7.4) carefully such that the cells were not detached. Then, 5004 KRH buffer containing 1 mM Ile-Leu, Ile-Trp, Ala-Leu, Val-Leu, Gly-Leu, Asp-Leu, Lys-Ile, Leu-Leu, Ile-Ile, Leu-Ile, Ile-Asn, Leu-Ala, Leu-Glu, Leu-Val or Ile-Val (Kokusan Chemical Co., Ltd.) was added to each well and reacted for 3 hours with the cells. Thereafter, the KRH buffer was removed, and 100 KRH buffer containing 8 mM 2-deoxyglucose was added to each well and reacted for accurately 10 minutes with for the cells. The reaction was terminated with 100 of 0.1 N NaOH, followed by neutralization with an equal volume of 0.1 N HCl, and then the amount of 2-deoxyglucose 6-phosphate in the cells was quantified by an enzymatic method to determine the rate of glucose uptake.

The rate of glucose uptake (average value±standard deviation) is shown in Table 9. Ile-Leu, Ile-Trp, Ala-Leu, Val-Leu, Gly-Leu, Asp-Leu, Lys-Ile, Leu-Leu, Ile-Ile, Leu-Ile, Ile-Asn, Leu-Ala, Leu-Glu, Leu-Val and Ile-Val had an action of glucose uptake into muscle cells.

TABLE 9

| | Rate of glucose uptake into muscle cells (nmol/min/well) |
|---|---|
| Control (with no sample added) | 1.21 ± 0.07 |
| 1 mM Ile-Leu | 1.61 ± 0.05* |
| 1 mM Ile-Trp | 1.91 ± 0.06* |
| 1 mM Ala-Leu | 1.91 ± 0.07* |
| 1 mM Val-Leu | 1.76 ± 0.07* |
| 1 mM Gly-Leu | 1.81 ± 0.04* |
| 1 mM Asp-Leu | 1.81 ± 0.50* |
| 1 mM Lys-Ile | 2.34 ± 0.06* |
| 1 mM Leu-Leu | 1.75 ± 0.05* |
| 1 mM Ile-Ile | 1.88 ± 0.05* |
| 1 mM Leu-Ile | 1.73 ± 0.04* |
| 1 mM Ile-Asn | 1.92 ± 0.06* |
| 1 mM Leu-Ala | 2.09 ± 0.08* |
| 1 mM Leu-Glu | 2.16 ± 0.05* |
| 1 mM Leu-Val | 1.74 ± 0.06* |
| 1 mM Ile-Val | 1.80 ± 0.07* |

*There is a significant difference within 5%.

Biological Test Example 7

Test for Confirmation of an Effect of Improving Endurance Performance in Mice Male C57BL/6J mice each weighing about 20 g (CLEA Japan, Inc.) were feed for 3 weeks with freely given water and food (8 mice per group). In the first week of feeding, the mice were subjected to treadmill exercise training under conditions starting from 15 meters/min. and 15 minutes without slope and then acclimated to treadmill exercise by gradually increasing the speed and exercise time to 22 meters/min. and 30 minutes respectively without slope. From the second week to the end of feeding, the mice were subjected to exercise training under the conditions of 22 meters/min. and 30 minutes without slope. The mice were subjected to this exercise training for 5 days per week. The mice were allowed to ingest 25% casein diet (in accordance with AIN93G), or 25% casein diet whose casein had been replaced by the milk whey protein hydrolysate prepared in Production Example 1. After 3 weeks of feeding, an exercise performance test was performed. The mice were subjected to exercise training with a treadmill under the condition of a speed of 30 meters/min. without slope, and the time until the mice became completely exhausted was measured.

The endurance time (average value±standard deviation) is shown in Table 10. The mice given the protein hydrolysate, as compared with the mice given the casein diet, increased the endurance time about 1.7-fold.

TABLE 10

|  | Endurance time (minutes) |
| --- | --- |
| 25% casein diet | 37 ± 9 |
| Protein hydrolysate feed | 63 ± 7* |

*There is a significant difference within 5%.

The composition of the present invention had a glucose uptake-promoting action in vitro and simultaneously had an action of preventing an elevation of blood glucose level, an effect of storing glycogen, and an effect of improving endurance performance even in the in vivo animal studies as shown above in the biological test examples.

The invention claimed is:

1. A composition for promoting glucose uptake, comprising dipeptides having an effect of promoting glucose uptake as the active ingredient, wherein the dipeptides consist of Ile-Leu, Leu-Ala, and at least one member selected from the group consisting of Ile-Trp, Ala-Leu, Val-Leu, Gly-Leu, Asp-Leu, Lys-Ile, Leu-Leu, Ile-Ile, Leu-Ile, Ile-Asn, Leu-Glu, Leu-Val, and Ile-Val.

2. A composition for promoting glucose uptake, comprising dipeptides having an effect of promoting glucose uptake as the active ingredient, wherein the dipeptides comprise Ile-Leu, Ile-Trp, Val-Leu, Leu-Ile, and at least one member selected from the group consisting of Ala-Leu, Gly-Leu, Asp-Leu, Lys-Ile, Leu-Leu, Ile-Ile, Ile-Asn, Leu-Ala, Leu-Glu, Leu-Val, and Ile-Val.

3. A composition for promoting glucose uptake, comprising dipeptides having an effect of promoting glucose uptake as the active ingredient, wherein the dipeptides consist of Ile-Leu, Leu-Leu, Ile-Ile, and at least one member selected from the group consisting of Ile-Trp, Ala-Leu, Val-Leu, Gly-Leu, Asp-Leu, Lys-Ile, Leu-Ile, Ile-Asn, Leu-Ala, Leu-Glu, Leu-Val, and Ile-Val.

4. A composition for promoting glucose uptake, comprising dipeptides having an effect of promoting glucose uptake as the active ingredient, wherein the dipeptides comprise Ile-Leu, Ile-Trp, Ala-Leu, Val-Leu, Gly-Leu, Asp-Leu, Lys-Ile, Leu-Leu, Ile-Ile, Leu-Ile, Ile-Asn, Leu-Ala, Leu-Glu, Leu-Val, and Ile-Val.

5. The composition according to claim 4, wherein the composition is a dipeptide-containing protein hydrolysate obtained by hydrolyzing a protein.

6. The composition according to claim 5, wherein an enzyme used in protein hydrolysis is a protease derived from *Aspergillus* and/or a protease derived from *Bacillus*.

7. The composition according to claim 6, wherein the enzyme used in protein hydrolysis is a combination of trypsin and/or pepsin in addition to a protease derived from *Aspergillus* and/or a protease derived from *Bacillus*.

8. The composition according to claim 5, wherein the protein is at least one member selected from the group consisting of casein, soybean protein, wheat gluten, milk whey protein, and beef.

9. The composition according to claim 4, wherein the dipeptide has an action of promoting glucose uptake into muscle cells.

10. A food which comprises the composition according to claim 1.

11. A food which comprises the composition according to claim 2.

12. A food which comprises the composition according to claim 3.

13. A food which comprises the composition according to claim 4.

14. A pharmaceutical composition which comprises the composition according to claim 4.

15. A method for preventing or treating diabetes mellitus or an elevation of blood glucose level by administering the composition according to claim 4.

16. A method for promoting glycogen storage in tissues by administering the composition according to claim 4.

17. A method for enhancing physical strength, enhancing athletic ability, improving endurance performance, or relieving fatigue by administering the composition according to claim 4.

18. A process for producing the composition according to claim 4, which comprises hydrolyzing a protein using an enzyme.

19. A process for producing the composition according to claim 16, wherein an enzyme used in protein hydrolysis is a protease derived from *Aspergillus* and/or a protease derived from *Bacillus*.

20. A process for producing the composition according to claim 17, wherein the enzyme used in protein hydrolysis is a combination of trypsin and/or pepsin in addition to a protease derived from *Aspergillus* and/or a protease derived from *Bacillus*.

* * * * *